(12) United States Patent
Hedrick

(10) Patent No.: US 7,884,255 B2
(45) Date of Patent: Feb. 8, 2011

(54) CHEMICAL PRODUCTION PROCESSES AND SYSTEMS

(76) Inventor: Vicki Hedrick, 9262 S. 300 E., Brookston, IN (US) 47923

( * ) Notice: Subject to any disclaimer, the term of this patent is extended or adjusted under 35 U.S.C. 154(b) by 0 days.

(21) Appl. No.: 11/661,166

(22) PCT Filed: Aug. 26, 2005

(86) PCT No.: PCT/US2005/030349

§ 371 (c)(1),
(2), (4) Date: Feb. 23, 2007

(87) PCT Pub. No.: WO2006/033771

PCT Pub. Date: Mar. 30, 2006

(65) Prior Publication Data

US 2007/0299287 A1      Dec. 27, 2007

Related U.S. Application Data

(60) Provisional application No. 60/605,232, filed on Aug. 26, 2004.

(51) Int. Cl.
*C07C 21/18* (2006.01)
*C07C 17/10* (2006.01)
(52) U.S. Cl. .................. 570/230; 570/135; 570/136
(58) Field of Classification Search .................. None
See application file for complete search history.

(56) References Cited

U.S. PATENT DOCUMENTS

| | | | |
|---|---|---|---|
| 2,802,887 A | 8/1957 | Miller et al. | |
| 3,564,064 A | 2/1971 | Nakagawa | |
| 4,003,941 A | 1/1977 | Crawford et al. | |
| 4,654,448 A | 3/1987 | Bargigia et al. | |
| 4,947,006 A | 8/1990 | Marraccini et al. | |
| 4,996,370 A | 2/1991 | Marraccini et al. | |
| 5,082,981 A | 1/1992 | Bargigia et al. | |
| 5,089,454 A | 2/1992 | Lerot et al. | |
| 5,243,103 A | 9/1993 | Lerot et al. | |
| 5,315,045 A * | 5/1994 | Berthe et al. ................. | 570/153 |
| 6,147,268 A | 11/2000 | Mueller et al. | |
| 6,544,319 B1 | 4/2003 | Krouse et al. | |
| 6,610,896 B2 | 8/2003 | Miki et al. | |

(Continued)

FOREIGN PATENT DOCUMENTS

CA         593529         3/1960

(Continued)

OTHER PUBLICATIONS

Sazonov et al., J. of Organometallics 681 (2003) 59-69.*

(Continued)

*Primary Examiner*—Karl J Puttlitz
(74) *Attorney, Agent, or Firm*—Wells St. John P.S.

(57) ABSTRACT

Chemical Production Processes and Systems. Chemical production processes are provided that include replacing a halogen of an unsaturated halocarbon to produce an unsaturated hydrohalocarbon. Chemical production systems are provided that include a reaction zone coupled to first and second reservoirs, the first reservoir containing an unsaturated halocarbon and the second reservoir containing a hydrogenating reagent with the system being configured to expose the unsaturated halocarbon of the first reservoir to the hydrogenating agent of the second reservoir within the reaction zone.

19 Claims, 1 Drawing Sheet

U.S. PATENT DOCUMENTS

| | | | |
|---|---|---|---|
| 2002/0193643 | A1 | 12/2002 | Miki et al. |
| 2003/0232922 | A1 | 12/2003 | Marchionni et al. |
| 2004/0022720 | A1 | 2/2004 | Low et al. |

FOREIGN PATENT DOCUMENTS

| | | | |
|---|---|---|---|
| CN | 1080277 | * | 1/1994 |
| DE | 2819209 | * | 11/1979 |
| EP | 0 053 657 A1 | | 6/1982 |
| EP | 0053657 | * | 6/1982 |
| EP | 0 343 707 | | 11/1989 |
| EP | 0 396 974 | | 11/1990 |
| EP | 05791273.5 | | 12/2008 |
| EP | 05792387.2 | | 12/2008 |
| FR | 2583039 | | 12/1986 |
| JP | 62252736 | | 11/1987 |
| JP | 01226831 | | 9/1989 |
| JP | 2017944 | | 1/1990 |
| JP | 2001114710 | | 4/2001 |
| JP | 2004026800 | | 1/2004 |
| WO | PCT/US05/030350 | | 1/2006 |
| WO | PCT/US05/030349 | | 4/2006 |
| WO | PCT/US05/030350 | | 8/2006 |

OTHER PUBLICATIONS

Catalysis Kirk-Othmer Encyclopedia of Chemical Technology Copyright © 2001, pp. 200-254.*

J. Donald Burton and Steven W. Hansen, "*The Stereospecific Preparation of E-Alkenyl Cadmium Reagents Directly From E-Alkenyl Iodides and Bromides and Cadmium Metal,*" Journal of Fluorine Chemistry, 31 (1986) p. 461-465.

Pamela L. Heinze and Donald J. Burton, "*Palladium-Catalyzed Cross-Coupling of Perfluoroalkenylzinc Reagents with Arl Iodides,*" Journal of Organic Chemistry, 1988, 53, p. 2714-2720.

Chongsoo Lim, Donald J. Burton, Craig A. Wesolowski, "*The stereospecific preparation of two perfluoro-1,3-butadiene synthons; (E)-1-trimethylsilyl-1,2,3,4,4-pentafluoro-1,3-butadiene and (E)-1-tributylstannyl-1,2,3,4,4-pentafluoro-1,3-butadiene,*" Journal of Fluorine Chemistry, 119 (2003) p. 21-26.

Database CAPLUS on STN, Chemical Abstract, Jiang et al., Competitive path in the addition reaction of perfluoroolefins, Youji Huaxue (1985), 5, 400-403.

Burton, et al., Journal of the American Chemical Society, vol. 108, 1986, pp. 4229-4230.

Database WPI, Thomson Scientific, London, AN 2001-484824 XP002507174.

Demiel, Arieh, Addition of Alcohols to Fluorinated Ethylenes, Journal of Organic Chemistry, vol. 25, 1960, pp. 993-996.

Dolbier Jr., et al., Kinetic and Thermodynamic Studies of the Thermal Electrocyclic Interconversions of Perfluorinated Dienes and Cyclobutenes, Journal of The American Chemical Society, vol. 109, 1987, pp. 219-225.

E. J. Soloski, et al., Synthesis of Trifluorovinylpolyhaloaryl Compounds via Polyhaloarylcopper Complexes, Journal of Fluorine Chemistry, vol. 2, No. 4, 1972/73, pp. 361-371.

Ling Xue, et al., A Novel Stereospecific Route to (E)- and (Z)-(2 Substituted-1,2-difluoroethenyl)stannanes, Journal of Organic Chemistry, vol. 62, 1997, pp. 1064-1071.

Martinet, et al., Journal of Organometallic Chemistry, 367 (1989) 1-10.

Park, et al., The Addition Products of Trifluoroethylene, Journal of the American Chemical Society, vol. 73, 1951, pp. 711-712.

Park, et al., The Preparation and Properties of Trifluoroiodoethene, Journal of The American Chemical Society, vol. 78, 1956, pp. 59-62.

* cited by examiner

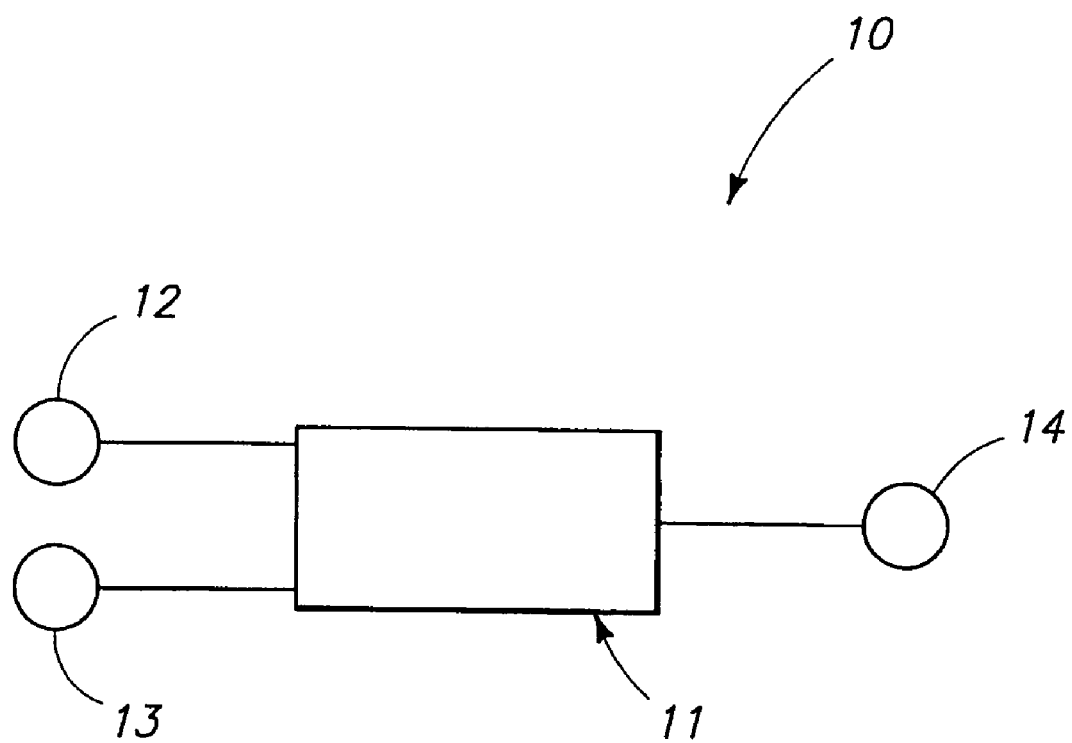

CHEMICAL PRODUCTION PROCESSES AND SYSTEMS

RELATED PATENT DATA

This application is a 35 U.S.C. §371 of and claims priority to PCT International Application Number PCT/U52005/030349 which was filed 26 Aug., 2005, and was published in English, which claims priority under 35 U.S.C. §119 to U.S. Provisional Patent Application No. 60/605,232 which was filed 26 Aug., 2004 the entirety of each are incorporated herein by reference.

TECHNICAL FIELD

The present invention relates to the field of chemical production processes and systems and more specifically to the production of hydrogenated olefins.

BACKGROUND

Hydrogenated olefins can be produced in numerous ways, including via elimination reactions for example. Hydrogenating an olefin, particularly halogenated olefins, can prove to be difficult for at least the reason that the drawback of hydrogenating an olefin is that the hydrogens typically add across the double bond saturating the compound. It can be beneficial to be able to add a hydrogen to an olefin without saturating the compound. The present invention provides chemical production processes and systems for hydrogenating olefins.

SUMMARY

Chemical production processes are provided that include replacing a halogen of an unsaturated halocarbon to produce an unsaturated hydrohalocarbon.

Chemical production systems are provided that include a reaction zone coupled to first and second reservoirs, the first reservoir containing an unsaturated halocarbon and the second reservoir containing a hydrogenating reagent with the system being configured to expose the unsaturated halocarbon of the first reservoir to the hydrogenating agent of the second reservoir within the reaction zone.

BRIEF DESCRIPTION OF THE FIGURE

The figure is an exemplary system for preparing compositions according to an embodiment.

DETAILED DESCRIPTION OF THE PREFERRED EMBODIMENTS

Chemical production processes and systems as described with reference to the Figure depicting a system 10 that includes a reaction zone 11 coupled to a halocarbon reservoir 12 and a hydrogenating reagent reservoir 13. System 10 further includes a product recovery reservoir 14.

The halocarbon of reservoir 12 can be a C-2 halocarbon, and in exemplary embodiments, the halocarbon can be a heterohalocarbon. For example, and by way of example only, the halocarbon can comprise both F and Cl, and, as another example, the halocarbon can comprise both F and Br. In exemplary embodiments, the halocarbon can also be

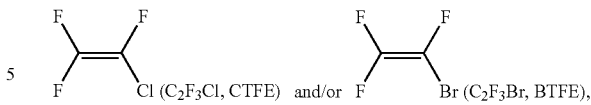

for example.

According to exemplary embodiments, the hydrogenating reagent from hydrogenating reagent reservoir 13 can be provided to reaction zone 11. According to exemplary embodiments, the hydrogenating reagent may include H, such as $H_2$. Reaction zone 11 can be coupled to reservoirs 13 and 14 via separate conduits with each conduit configured to control the flow of the contents of the reservoirs to reaction zone 11. The conduits may be equipped with flow meters, for example. Both the halocarbon and the hydrogenating reagent may be provided to the reaction zone at a mole ratio of hydrogenating reagent to halocarbon utilizing the flow meters. For example, the mole ratio of hydrogenating reagent to halocarbon may be from about 0.66 to about 11. By way of another example, the mole ratio may be at least about 0.66 and/or the mole ratio may be less than 11. In another exemplary embodiment, the mole ratio may be at least about 1.8.

Reaction zone 11 can include a single and/or multiple reactors. A reactor within reaction zone 11 can be constructed of a nickel-alloy such as an Inconel® (Tevo Industries 9337 Ravenna Rd. Twinsburg, Ohio 44087) tube having a volume of 34 cc (OD=0.5", length=14.125", wall thickness=0.035") equipped with a pressure gauge, pressure relief valve, Matheson Gas rotometers for gas feeds, and/or a vaporizer, for example.

Reaction zone 11 may include a catalyst composition within a reactor. The catalyst composition may comprise a catalyst support and/or the catalyst composition may comprise activated carbon. The catalyst composition provided within reaction zone 11 may comprise one or more Pd, Cu, and/or Ni and/or the catalyst composition may comprise both Pd and Cu. Where the catalyst composition comprises both Pd and Cu, the composition may include at least about 0.6% (wt./wt.) Pd and/or the composition may be at least about 5.5% (wt./wt.) Cu. In accordance with other embodiments, the catalyst composition may comprise nickel and nickel may be at least about 5% (wt./wt.) of the composition. Additional catalyst compositions can include:; Pricat CZ 29/4, $Al_2O_3$, ZnO, CuO, (Synetix (PO Box 1, Billingham, Cleveland, TS23 1 LB, UK); 7% $FeCl_3$ on Takeda Carbon (Life-Environment Company, 12-10, Nlhonbashi 2-chamo Chuo-ku, Tokyo 103-8868, Japan); $FeCl_3$ (in-house,and/or $ZnCl_2$ (in-house); and those obtained from Engelhard (Chemical Catalysts Group, 554 Engelhard Drive, Seneca, S.C. 29678), such as,0.6% Pd/5.5% Cu and/or Ni (Engelhard, 5% Ni on 1.5 mm carbon).

Prior to providing the halocarbon and/or the hydrogenating agent from reservoirs 12 and 13, respectively, a reactor of reaction zone 11 may be packed with the catalyst composition and heated to a temperature and/or exposed to a reducing agent for a sufficient time to activate the catalyst composition. Activation of the catalyst composition may be performed over a period of from about an hour to about 24 hours, for example. Typically, the catalyst composition within the reactor may be heated to from about 150° C. to about 300° C. during the activation. The catalyst composition may also be re-activated intermittently during the process at temperatures of from about 150° C. to 400° C.

The halocarbon and hydrogenating reagent may be formed into a mixture within the reactor and a portion of the mixture may be heated to at least 300° C. According to an exemplary embodiment, the portion may be heated to from about 300° C. and to about 400° C. The portion may also be heated to greater than about 400° C., for example. The temperature within the reaction zone can also be from 150° C. to 475° C. when providing mole ratios of reducing-reagent to halocarbon of 0.1 to 10.0. The reactants can reside within reaction zone 11 to provide contact times of from about 2 to about 20 seconds and reducing-reagent flow rates can be from 25-100 cc/min while the halocarbon flow. rates can be from 8-410 cc/min.

Products leaving the reactor can be captured and/or further processed within product recovery reservoir 14. Reservoir 14 can include an apparatus such as a 10% KOH scrubber, a Drierite tube, and/or a dry ice/ acetone trap, for example. Exemplary products include, but are not limited to, unsaturated hydrohalocarbons including C-2 hydrohalocarbons. For example, and by way of example only, the hydrohalocarbon can comprise both F and H. In exemplary embodiments, the hydrohalocarbon can be trifluoroethylene ($C_2F_3H$, TriFE), and/or

for example. As such system 10 can be used to replace a halogen of an unsaturated halocarbon to produce an unsaturated hydrohalocarbon.

Exemplary schemes 1 and 2 demonstrate exemplary reactions that can be performed utilizing system 10 of the Figure.

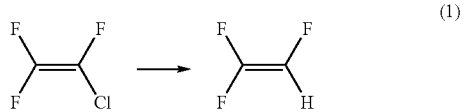
(1)

According to scheme (1) above, an Inconel tube can be packed with 0.6% Pd/5.5% Cu catalyst on activated carbon and maintained at 400° C. The reactants can be provided to the tube at a 4.5 mole ratio of $H_2$ to CTFE and exposed to the catalyst for a 9.6 second contact time. The conversion of CTFE to TriFE can be about 30.3% and selectivity can be 83.5% as determined by gas chromatography.

According to another embodiment, the Inconel tube can be packed with a Ni (Engelhard, 5% Ni on 1.5 mm carbon) catalyst and maintained at 350° C. The reactants can be provided to the tube at a 0.66 mole ratio of $H_2$ to CTFE and exposed to the catalyst for an 11.2 second contact time. The conversion of CTFE to TriFE can be about 50.1% and the selectivity can be 61.1% as determined by gas chromatography.

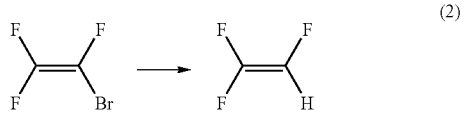
(2)

According to scheme (2) above, an Inconel tube can be packed with the 0.6% Pd/5.5% Cu catalyst on activated carbon and maintained at 300° C. The reactants can be provided to the tube at a 4.5 mole ratio of $H_2$ to BTFE and can be exposed to the catalyst for a 19.6 second contact time. The conversion of BTFE to TriFE can be 72.3% and selectivity can be 87.0% as determined by gas chromatography.

According to still another embodiment, an Inconel tube can be packed with the Ni (Engelhard, 5% Ni on 1.5 mm carbon) catalyst and maintained at 400° C. The reactants can be provided to the tube at a 1.8 mole ratio of $H_2$ to BTFE and can be exposed to the catalyst for a 12.9 second contact time. The conversion of BTFE to TriFE can be 96.8% and selectivity can be 90.7% as determined by gas chromatography.

What is claimed is:

1. A chemical production process comprising replacing one or both of a Cl and a Br of one or both of $C_2F_3Cl$ and $C_2F_3Br$ in the presence of both a hydrogenating reagent and a catalyst comprising Cu and Pd to produce an unsaturated hydrohalocarbon, the catalyst comprising Cu at a weight percent greater than a weight percent of Pd.

2. The chemical production process of claim 1 wherein the replacing comprises:
   providing the halocarbon to within a reactor;
   providing a hydrogenating reagent to within the reactor; and
   recovering the hydrohalocarbon from the reactor.

3. The chemical production process of claim 2 wherein the halocarbon and the hydrogenating reagent are provided to within the reactor at a mole ratio of hydrogenating reagent to halocarbon, the mole ratio being from about 0.1 to about 11.

4. The chemical production process of claim 2 wherein the one or both of $C_2F_3Cl$ and $C_2F_3Br$ and the hydrogenating reagent are provided to within the reactor at a mole ratio of hydrogenating reagent to one or both of $C_2F_3Cl$ and $C_2F_3Br$, the mole ratio being at least 0.1.

5. The chemical production process of claim 2 wherein the one or both of $C_2F_3Cl$ and $C_2F_3Br$ and the hydrogenating reagent are provided to within the reactor at a mole ratio of hydrogenating reagent to one or both of $C_2F_3Cl$ and $C_2F_3Br$, the mole ratio being less than 11.

6. The chemical production process of claim 2 wherein the one or both of $C_2F_3Cl$ and $C_2F_3Br$ and the hydrogenating reagent are provided to within the reactor at a mole ratio of hydrogenating reagent to one or both of $C_2F_3Cl$ and $C_2F_3Br$, the mole ratio being at least 1.8.

7. The chemical production process of claim 2 wherein the hydrogenating reagent comprises H.

8. The chemical production process of claim 2 wherein the hydrogenating reagent is $H_2$.

9. The chemical production process of claim 2 further comprising providing a catalyst composition to within the reactor.

10. The chemical production process of claim 9 wherein the catalyst composition comprises a catalyst support.

11. The chemical production process of claim 9 wherein the catalyst composition comprises activated carbon.

12. The chemical production process of claim 1 wherein the Pd is at least about 0.6% (wt./wt.) of the catalyst.

13. The chemical production process of claim 1 wherein the Cu is at least about 5.5% (wt./wt.) of the catalyst.

14. The chemical production process of claim 2 wherein the reactor is constructed of a nickel alloy.

15. The chemical production process of claim 2 further comprising:
   forming a mixture comprising the halocarbon and the hydrogenating reagent within the reactor; and
   heating a portion of the mixture to at least about 475° C.

16. The chemical production process of claim 2 further comprising:

forming a mixture comprising the one or both of $C_2F_3Cl$ and $C_2F_3Br$ and the hydrogenating reagent within the reactor; and heating a portion of the mixture to from about 150° C. to about 400° C.

17. The chemical production process of claim 2 further comprising:

forming a mixture comprising the one or both of $C_2F_3Cl$ and $C_2F_3Br$ and the hydrogenating reagent within the reactor; and heating a portion of the mixture to at least about 400° C.

18. The chemical production process of claim 2 further comprising:

forming a mixture comprising the one or both of $C_2F_3Cl$ and $C_2F_3Br$ and the hydrogenating reagent within the reactor; and heating a portion of the mixture to at least about 300° C.

19. The chemical production process of claim 2 further comprising:

forming a mixture comprising the one or both of $C_2F_3Cl$ and $C_2F_3Br$ and the hydrogenating reagent within the reactor; and heating a portion of the mixture to from about 300° C. to about 400° C.

\* \* \* \* \*

UNITED STATES PATENT AND TRADEMARK OFFICE
CERTIFICATE OF CORRECTION

PATENT NO. : 7,884,255 B2
APPLICATION NO. : 11/661166
DATED : February 8, 2011
INVENTOR(S) : Vicki Hendrick Page 1 of 2

It is certified that error appears in the above-identified patent and that said Letters Patent is hereby corrected as shown below:

Title Page, (56) References Cited – Remove "EP 0053657 6/1982" (duplicate listing)

Column 2, line 47 – Replace "(Synetix (PO Box 1, Billingham, Cleveland, TS23 1 LB, UK);" with --(Synetix (PO Box 1, Billingham, Cleveland, TS23 1 LB, UK));--

Column 2, line 50 – Replace "(in-house, and" with --(in-house) and--

Column 4, line 20 (Claim 2) – Replace "the halocarbon to" with --the one or both of $C_2F_3Cl$ and $C_2F_3Br$ to--

Column 4, line 25 (Claim 3) – Replace "the halocarbon and" with --the one or both of $C_2F_3Cl$ and $C_2F_3Br$ and--

Column 4, line 27 (Claim 3) – Replace "to halocarbon, the" with --to one or both of $C_2F_3Cl$ and $C_2F_3Br$, the--

Column 4, line 48 (Claim 9) – Replace "providing a catalyst composition to" with --providing the catalyst to--

Column 4, line 51 (Claim 10) – Replace "the catalyst composition comprises" with --the catalyst comprises--

Column 4, line 53 (Claim 11) – Replace "the catalyst composition comprises" with --the catalyst comprises--

Signed and Sealed this
Thirty-first Day of July, 2012

David J. Kappos
*Director of the United States Patent and Trademark Office*

CERTIFICATE OF CORRECTION (continued)
U.S. Pat. No. 7,884,255 B2

Column 4, line 62 (Claim 15) – Replace "the halocarbon and" with --the one or both of $C_2F_3Cl$ and $C_2F_3Br$ and--

Column 4, line 64 (Claim 15) – Replace "about 475°C." with --300°C.--